United States Patent
Rice et al.

(10) Patent No.: US 11,628,094 B2
(45) Date of Patent: Apr. 18, 2023

(54) WOUND DRESSING FOR WOUND VOLUME ESTIMATION

(71) Applicant: KCI LICENSING, INC., San Antonio, TX (US)

(72) Inventors: Justin R. Rice, San Antonio, TX (US); Christopher A. Carroll, San Antonio, TX (US); Benjamin A. Pratt, Wimborne (GB); Shannon C. Ingram, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 164 days.

(21) Appl. No.: 17/253,263

(22) PCT Filed: Jun. 11, 2019

(86) PCT No.: PCT/US2019/036598
§ 371 (c)(1),
(2) Date: Dec. 17, 2020

(87) PCT Pub. No.: WO2020/005536
PCT Pub. Date: Jan. 2, 2020

(65) Prior Publication Data
US 2021/0113748 A1 Apr. 22, 2021

Related U.S. Application Data

(60) Provisional application No. 62/690,609, filed on Jun. 27, 2018.

(51) Int. Cl.
*A61F 13/00* (2006.01)
*A61F 13/02* (2006.01)
*A61M 1/00* (2006.01)

(52) U.S. Cl.
CPC .. *A61F 13/00068* (2013.01); *A61F 13/00055* (2013.01); *A61F 13/0216* (2013.01);
(Continued)

(58) Field of Classification Search
CPC ...... A61F 13/00068; A61F 2013/00842; A61F 2013/0017; A61M 1/0058; A61M 1/90;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, Md and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Adam Marcetich
*Assistant Examiner* — Meagan Ngo (57) ABSTRACT

A wound therapy system includes a therapy unit, a wound dressing and an optional controller. The therapy unit is configured to deliver instillation fluid to a wound site. The wound dressing is formed from a plurality of discrete, individual blocks that are selectively separable from one another along a plurality of separation-lines, allowing the wound dressing to be customized to the shape and size of the wound site. By calculating the remaining blocks that define the wound dressing following customization, the volume of
(Continued)

the wound dressing may be determined. The controller may be configured to deliver fluid to the wound site based on this calculated volume. The controller may also optionally be used to gauge the healing of the wound site over time by monitoring the changes in volume of customized wound dressings as wound dressings are replaced during the course of treatment of the wound site.

23 Claims, 4 Drawing Sheets (52) U.S. Cl.
CPC ......... *A61F 13/0223* (2013.01); *A61M 1/915* (2021.05); *A61M 1/92* (2021.05); *A61M 1/962* (2021.05); *A61M 2205/3379* (2013.01); *A61M 2205/502* (2013.01)

(58) Field of Classification Search
CPC ...... A61M 1/92; A61M 1/915; A61M 31/002; A61M 2205/3334; A61M 5/168; A61B 2217/005; A61B 2217/007; A61B 1/015
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0041401 A1* | 2/2008 | Casola | A61M 1/74 128/897 |
| 2009/0227969 A1 | 9/2009 | Jaeb et al. | |
| 2011/0224634 A1 | 9/2011 | Locke et al. | |
| 2011/0319804 A1* | 12/2011 | Greener | A61F 13/00987 83/13 |
| 2015/0165182 A1* | 6/2015 | Pratt | A61M 39/22 604/290 |
| 2016/0166744 A1* | 6/2016 | Hartwell | A61M 1/915 604/319 |
| 2018/0050137 A1* | 2/2018 | Ryu | A61M 1/74 |
| 2019/0336345 A1* | 11/2019 | Bannwart | A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |

(56) References Cited

FOREIGN PATENT DOCUMENTS

| | | |
|---|---|---|
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2015/008054 A1 | 1/2015 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
*George V. Letsou, Md.*, et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sept. 3, 1997.
Dattilo, Philip P., Jr, et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P. "Irrigation Treatment of Leg Ulcers", The Lancet, Sep. 3, 1983, pp. 532-534.
Chinn, Steven D et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

(56) References Cited

OTHER PUBLICATIONS

International Search Report and Written Opinion in International Application No. PCT/US2019/036598, dated Sep. 12, 2019.

\* cited by examiner

WOUND DRESSING FOR WOUND VOLUME ESTIMATION

CROSS-REFERENCE TO RELATED APPLICATIONS

This Application claims the benefit of priority to international patent application number PCT/US2019/036598, filed on Jun. 11, 2019, which claims the benefit of priority to U.S. Provisional Application No. 62/690,609, filed on Jun. 27, 2018, the complete disclosures of which are incorporated herein by reference in their entireties.

BACKGROUND

The present disclosure relates generally to a wound dressing, and more particularly to a customizable wound dressing configured to estimate the volume of a wound.

Negative pressure wound therapy (NPWT) is a type of wound therapy that involves applying a negative pressure to a wound site to promote wound healing. Some wound treatment systems apply negative pressure to a wound using a pneumatic pump to generate the negative pressure and flow required. Recent advancements in wound healing with NPWT involve applying topical fluids to wounds to work in combination with NPWT. However, it can be difficult to determine the appropriate volume of instillation fluid to deliver to the wound. Additionally, it can be difficult to accurately monitor and track healing progression over time.

SUMMARY

One implementation of the present disclosure is a wound therapy system including a manifold for placement in a wound and a therapy device. The manifold includes a plurality of intersecting perforations that divide the manifold into a plurality of discrete blocks and facilitate separating one or more of the discrete blocks from a remainder of the discrete blocks. The therapy device includes a pump, a user interface and a controller. The pump is operable to deliver an instillation fluid to the wound dressing. The user interface is configured to receive user input indicating a number of the one or more discrete blocks separated from the remainder of the discrete blocks. The controller is configured to determine a volume of the instillation fluid to deliver to the manifold based on the user input and to operate the pump to deliver the determined volume of the instillation fluid to the manifold.

In some embodiments, the manifold includes a wound interface layer configured to contact a wound. The plurality of intersecting perforations extend through the wound interface layer. In some embodiments, the manifold includes a cover layer coupled to the wound interface layer. The plurality of intersecting perforations extend through both the cover layer and the wound interface layer. In some embodiments, the cover layer includes a polyurethane film laminated to the wound interface layer.

In some embodiments, the wound dressing includes a wound interface layer and a cover layer. The wound interface layer is configured to contact a wound. The cover layer is coupled to the wound interface layer. A plurality of holes extend through the wound interface layer and the cover layer.

In some embodiments, each perforation of the plurality of intersecting perforations has a perforation size defining a size of the perforation. The wound dressing includes a plurality of holes that extend through the wound dressing, each of the holes having a hole size larger than the perforation size. In some embodiments, the plurality of holes are located at intersections of the plurality of intersecting perforations. In some embodiments, the plurality of holes are located within the plurality of discrete blocks offset from the plurality of intersecting perforations.

In some embodiments, one or more of the plurality of discrete blocks is triangular. In some embodiments, one or more of the plurality of discrete blocks is rectangular. In some embodiments, the plurality of discrete blocks include at least one triangular block and at least one rectangular block.

In some embodiments, the controller is configured to use the number of the discrete blocks separated from the remainder of the discrete blocks to determine the volume of the instillation fluid to deliver to the wound dressing. In some embodiments, the user input indicates both the number of the discrete blocks separated from remainder of the discrete blocks and a type of the wound dressing. The controller is configured to use both the number of the discrete blocks separated from remainder of the discrete blocks and the type of the wound dressing to determine the volume of the instillation fluid to deliver to the wound dressing.

In some embodiments, the controller is configured to estimate a wound volume based on the number of discrete blocks indicated by the user input and determine the volume of instillation fluid to deliver to the wound dressing based on the estimated wound volume. In some embodiments, the controller is configured to estimate the wound volume at a plurality of times during wound treatment and determine healing progression based on changes in the estimated wound volume during wound treatment. In some embodiments, the controller is configured to determine the volume of instillation fluid to deliver to the wound dressing by multiplying the estimated wound volume by a fluid instillation factor. In some embodiments, the fluid instillation factor is less than one such that less than a total volume of the wound dressing is filled with the instillation fluid. In some embodiments, the fluid instillation factor is between approximately 0.2 and approximately 0.8.

In some embodiments, tubing fluidly couples the pump with the wound dressing. The pump delivers the determined volume of the instillation fluid to the manifold via the tubing. In some embodiments, the controller is configured to operate the pump to apply negative pressure to the manifold.

One implementation of the present disclosure is a wound therapy system including a wound dressing and a therapy device. The wound dressing includes a plurality of intersecting delineations that divide the wound dressing into a plurality of discrete blocks and facilitate separating one or more of the discrete blocks from a remainder of the discrete blocks along the delineations. The therapy device includes a pump, a user interface and a controller. The pump is operable to deliver an instillation fluid to the wound dressing. The user interface is configured to receive user input indicating a number of the one or more discrete blocks separated from the remainder of the discrete blocks. The controller is configured to determine a volume of the instillation fluid to deliver to the wound dressing based on the user input and to operate the pump to deliver the determined volume of the instillation fluid to the wound dressing.

In some embodiments, the plurality of intersecting delineations include welds that extend at least partially through the wound dressing. In some embodiments, the plurality of intersecting delineations include perforations that extend at least partially through the wound dressing. In some embodiments, the plurality of intersecting delineations comprise markings that extend along a surface of the wound dressing.

In some embodiments, the wound dressing includes a wound interface layer configured to contact a wound. The plurality of intersecting delineations extend through the wound interface layer. In some embodiments, the wound dressing includes a cover layer coupled to the wound interface layer. The plurality of intersecting delineations extend through both the cover layer and the wound interface layer. In some embodiments, the cover layer includes a polyurethane film laminated to the wound interface layer.

In some embodiments, the wound dressing includes a wound interface and a cover layer. The wound interface layer is configured to contact a wound. The cover layer is coupled to the wound interface layer. A plurality of holes extend through the wound interface layer and the cover layer.

In some embodiments, each delineation of the plurality of intersecting delineation has a delineation size defining a size of the delineation. The wound dressing includes a plurality of holes that extend through the wound dressing, each of the holes having a hole size larger than the delineation size. In some embodiments, the plurality of holes are located at intersections of the plurality of intersecting delineations. In some embodiments, the plurality of holes are located within the plurality of discrete blocks offset from the plurality of intersecting delineations.

In some embodiments, one or more of the plurality of discrete blocks is triangular. In some embodiments, one or more of the plurality of discrete blocks is rectangular. In some embodiments, the plurality of discrete blocks include at least one triangular block and at least one rectangular block.

In some embodiments, the controller is configured to use the number of the discrete blocks separated from the remainder of the discrete blocks to determine the volume of the instillation fluid to deliver to the wound dressing. In some embodiments, the user input indicates both the number of the discrete blocks separated from remainder of the discrete blocks and a type of the wound dressing. The controller is configured to use both the number of the discrete blocks separated from remainder of the discrete blocks and the type of the wound dressing to determine the volume of the instillation fluid to deliver to the wound dressing.

In some embodiments, the controller is configured to estimate a wound volume based on the number of discrete blocks indicated by the user input and determine the volume of instillation fluid to deliver to the wound dressing based on the estimated wound volume. In some embodiments, the controller is configured to estimate the wound volume at a plurality of times during wound treatment and determine healing progression based on changes in the estimated wound volume during wound treatment. In some embodiments, the controller is configured to determine the volume of instillation fluid to deliver to the wound dressing by multiplying the estimated wound volume a fluid instillation factor. In some embodiments, the fluid instillation factor is less than one such that less than a total volume of the wound dressing is filled with the instillation fluid. In some embodiments, the fluid instillation factor is between approximately 0.2 and approximately 0.8.

In some embodiments, tubing fluidly couples the pump with the wound dressing. The pump delivers the determined volume of the instillation fluid to the wound dressing via the tubing. In some embodiments, the controller is configured to operate the pump to apply negative pressure to the wound dressing.

One implementation of the present disclosure is a method for delivering instillation fluid to a wound. One or more discrete blocks of a wound dressing are separated from a remainder of the discrete blocks along delineations of the wound dressing. A user input indicating a number of the discrete blocks separated from the reminder of the discrete blocks at a user interface of a wound therapy device is received. The wound therapy device determines a volume of instillation fluid to deliver to the wound dressing based on the user input. A pump of the wound therapy device is operated to deliver the determined volume of the instillation fluid to the wound.

In some embodiments, the delineations facilitate separating the one or more of the discrete blocks from the remainder of the discrete blocks along the delineations.

In some embodiments, a plurality of intersecting delineations are formed by applying, to the wound dressing, a plurality of intersecting welds that extend at least partially through the wound dressing. In some embodiments, the plurality of intersecting delineations are formed by applying, to the wound dressing, a plurality of intersecting perforations that extend at least partially through the wound dressing. In some embodiments, the plurality of intersecting delineations are formed by applying, to the wound dressing, a plurality of intersecting markings that extend along a surface of the wound dressing.

One implementation of the present disclosure is a wound dressing for use in a fluid instillation system. The wound dressing includes a wound interface layer configured to contact a wound. A plurality of intersecting delineations divide the wound interface layer into a plurality of discrete blocks and facilitate separating one or more of the discrete blocks from a remainder of the discrete blocks along the delineations.

In some embodiments, the plurality of intersecting delineations include welds that extend at least partially through the wound interface layer. In some embodiments, the plurality of intersecting delineations include perforations that extend at least partially through the wound interface layer. In some embodiments, the plurality of intersecting delineations include markings that extend along a surface of the wound dressing.

In some embodiments, a cover layer is coupled to the wound interface layer. The plurality of intersecting delineations extend through both the cover layer and the wound interface layer. In some embodiments, the cover layer includes a polyurethane film laminated to the wound interface layer. In some embodiments, a plurality of holes that extend through the wound interface layer and the cover layer.

In some embodiments, each delineation of the plurality of intersecting delineation has a delineation size defining a size of the delineation. The wound dressing further includes a plurality of holes that extend through the wound interface layer, each of the holes having a hole size larger than the delineation size. In some embodiments, the plurality of holes are located at intersections of the plurality of intersecting delineations. In some embodiments, the plurality of holes are located within the plurality of discrete blocks offset from the plurality of intersecting delineations.

In some embodiments, one or more of the plurality of discrete blocks is triangular. In some embodiments, one or more of the plurality of discrete blocks is rectangular. In some embodiments, the plurality of discrete blocks include at least one triangular block and at least one rectangular block.

In some embodiments, the wound dressing includes a wound interface layer configured to contact a wound. The method includes forming a plurality of intersecting delineations that extend through the wound interface layer. In some embodiments, the wound dressing includes a cover layer coupled to the wound interface layer. A plurality of intersecting delineations are formed that extend through both the cover layer and the wound interface layer. In some embodiments, the cover layer comprises a polyurethane film. The cover layer is laminated to the wound interface layer.

In some embodiments, the wound dressing includes a wound interface layer configured to contact a wound and a cover layer coupled to the wound interface layer. A plurality of holes are formed that extend through the wound interface layer and the cover layer. In some embodiments, wherein each delineation of the plurality of intersecting delineation has a delineation size defining a size of the delineation. A plurality of holes are formed that extend through the wound dressing, each of the holes having a hole size larger than the delineation size. In some embodiments, the plurality of holes are located at intersections of the plurality of intersecting delineations. In some embodiments, the plurality of holes are located within the plurality of discrete blocks offset from the plurality of intersecting delineations.

In some embodiments, one or more of the plurality of discrete blocks is triangular. In some embodiments, one or more of the plurality of discrete blocks is rectangular. In some embodiments, at least one triangular block and at least one rectangular block.

In some embodiments, the number of the discrete blocks separated from the remainder of the discrete blocks is used to determine the volume of the installation fluid to deliver to the wound dressing. In some embodiments, the user input indicates both the number of the discrete blocks separated from remainder of the discrete blocks and a type of the wound dressing. Both the number of the discrete blocks separated from remainder of the discrete blocks and the type of the wound dressing are used to determine the volume of the installation fluid to deliver to the wound dressing. In some embodiments, a wound volume is estimated based on the number of discrete blocks indicated by the user input. The volume of installation fluid to deliver to the wound dressing is determined based on the estimated wound volume.

In some embodiments, the wound volume is estimated at a plurality of times during wound treatment. Healing progression is determined based on changes in the estimated wound volume during wound treatment. In some embodiments, the volume of installation fluid to deliver to the wound dressing is determined by multiplying the estimated wound volume a fluid installation factor. In some embodiments, the fluid installation factor is less than one such that less than a total volume of the wound dressing is filled with the installation fluid. In some embodiments, the fluid installation factor is between approximately 0.2 and approximately 0.8.

In some embodiments, the pump is fluidly coupled with the wound dressing via tubing. The pump delivers the determined volume of the installation fluid to the wound dressing via the tubing. In some embodiments, the pump is operated to apply negative pressure to the wound dressing.

One implementation of the present disclosure is a method monitoring the healing of a wound. One or more discrete blocks of a first wound dressing are separated from a remainder of the discrete blocks along delineations of the first wound dressing. The one or more discrete blocks are selectively separated such that the remainder of discrete blocks define a modified first wound dressing having a shape and size that substantially corresponds to a shape and size of the wound. User input indicating a number of the discrete blocks separated from the remainder of the discrete blocks of the first wound dressing is received at a user interface of a wound therapy device. The wound therapy device calculates a first volume of the wound based on the number of remaining blocks defining the modified first wound dressing.

In some embodiments, the wound therapy device determines a first volume of installation fluid to deliver to the modified first wound dressing based on the calculated first volume of the wound. The modified first wound dressing is placed in the wound. A pump of the wound therapy device is operated to deliver the determined first volume of the installation fluid to the wound.

In some embodiments, the modified first wound dressing is removed from the wound. One or more discrete blocks of a second wound dressing are separated from a remainder of the discrete blocks along delineations of the second wound dressing. The one or more discrete blocks are selectively separated such that the remainder of discrete blocks define a modified second wound dressing having a shape and size that substantially corresponds to a shape and size of the wound. A user input indicating a number of the discrete blocks separated from the remainder of the discrete blocks of the second wound dressing is received at the user interface of the wound therapy device. The wound therapy device calculates a second volume of the wound based on the number of remaining blocks defining the modified second wound dressing.

In some embodiments, a healing rate of the wound is determined by comparing the difference between the second volume of the wound and the first volume of the wound to a length of time measured between the operation the pump of the wound therapy device to deliver the determined first volume of the installation fluid to the wound and removing the modified first wound dressing from the wound.

In some embodiments the wound therapy device determines a second volume of installation fluid to deliver to the modified first wound dressing based on the calculated second volume of the wound. The modified second wound dressing is placed in the wound. The pump of the wound therapy device is operated to deliver the determined second volume of the installation fluid to the wound.

In some embodiments, the modified second wound dressing is removed from the wound. One or more discrete blocks of a third wound dressing are separated from a remainder of the discrete blocks along delineations of the third wound dressing. The one or more discrete blocks are selectively separated such that the remainder of discrete blocks define a modified third wound dressing having a shape and size that substantially corresponds to a shape and size of the wound. User input indicating a number of the discrete blocks separated from the remainder of the discrete blocks of the third wound dressing is received at the user interface of the wound therapy device. The wound therapy device calculates a third volume of the wound based on the number of remaining blocks defining the modified third wound dressing.

In some embodiments, a projected third volume of a wound is calculated based on the calculated healing rate. In some embodiments, the calculated third volume is comparted to the calculated projected third volume.

Those skilled in the art will appreciate that the summary is illustrative only and is not intended to be in any way limiting. Other aspects, inventive features, and advantages of the devices and/or processes described herein, as defined

DETAILED DESCRIPTION

Referring generally to the FIGURES, a wound therapy system is shown according to various exemplary embodiments. The wound therapy system may include a therapy device, a wound dressing, and a controller. The therapy device may include an installation fluid canister, a removed fluid canister, a pneumatic pump, and an installation and a pump.

The wound dressing is configured to be applied to a patient's skin surrounding a wound. Following attachment of the wound dressing to the patient's skin, the therapy device may be configured to deliver instillation fluid to the wound and provide negative pressure wound therapy (NPWT) by maintaining the wound at negative pressure. Components of the wound therapy device, the wound dressing, and/or the wound site form a negative pressure circuit.

The wound dressing may be configured to be easily and quickly adjusted to the size and/or shape of the specific wound that is to be treated. In addition to providing a customized fit of the wound dressing to the wound site, the adjustable configuration of the wound dressing may provide for an easy estimation of the volume of the wound being treated. In some embodiments, the controller may be configured to utilize this estimated volume to determine the volume of instillation fluid to be delivered during treatment and/or to monitor the healing progression of the wound over time.

Wound Therapy System

Figure 1:
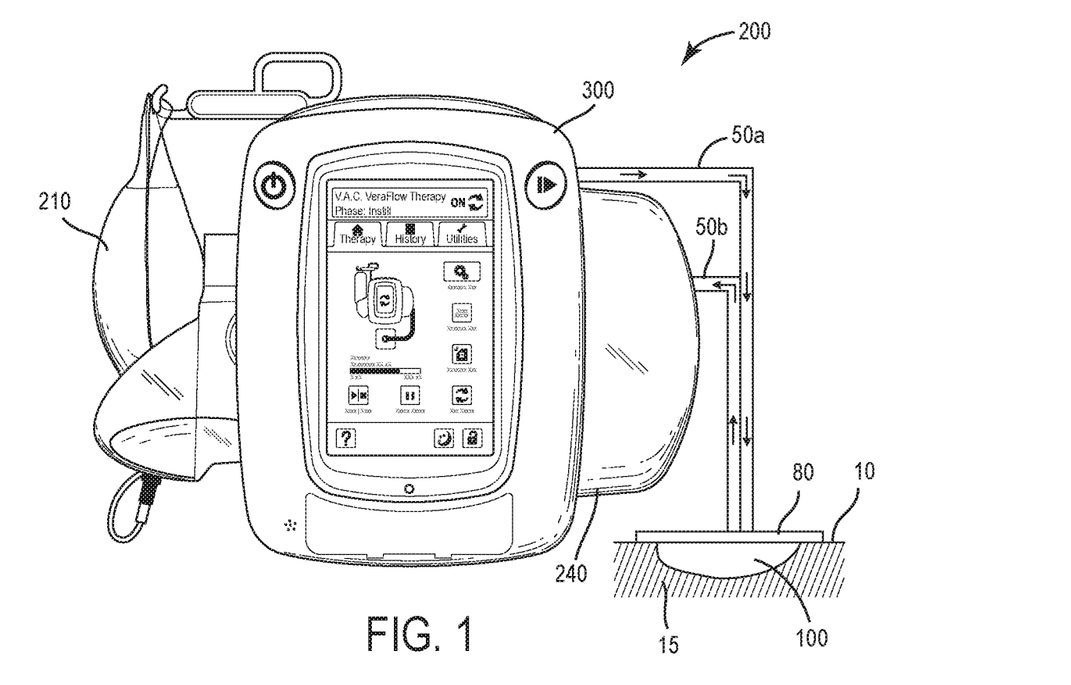
FIG. 1 is a block diagram of a wound therapy system including a therapy device coupled to a wound dressing via tubing, according to one embodiment.

Referring to FIG. 1 a wound therapy system 1 is shown according to an exemplary embodiment. The wound therapy system 1 is shown to include a therapy device 200 fluidly connected to a wound dressing 100 via tubing 50. A manifold configured to be placed in a wound site 15, such as, e.g. a wound dressing 100 may be adhered or sealed to a patient's skin 10 surrounding a wound site 15. A controller 300 configured to control and/or monitor the operation of the therapy device 200 may be operatively connected to the therapy device 200 via a wired or wireless connection.

a. Therapy Device

The therapy device 200 of the wound therapy system 1 may be configured to deliver an instillation fluid such as, e.g., a cleansing fluid, a prescribed fluid, a medicated fluid, an antibiotic fluid, saline, or any other type of fluid to a wound site 15 during wound treatment to assist with the healing of the wound site 15. The instillation fluid may be stored in an instillation fluid canister 210 and may be dispensed to the wound site 15 via instillation fluid tubing 50a extending between the instillation fluid canister 210 and the wound dressing 100 in response to the operation of an instillation pump (not shown). In some embodiments, instillation fluid canister 210 may be detachable from therapy device 200 to allow the instillation fluid canister 210 to be refilled and replaced as needed.

According to various embodiments, such as, e.g. the embodiment of wound therapy system 1 illustrated in FIG. 1, the therapy device 200 may be configured to provide negative pressure wound therapy ("NPWT") in addition to providing instillation therapy. In such embodiments, the therapy device 200 may include a negative pressure pump (not shown) configured to reduce the pressure at wound site 15 (relative to atmospheric pressure) by removing wound exudate, air, and other fluids from wound site 15. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 15 may include instillation fluid previously delivered to wound site 15 via, e.g. the instillation pump.

The fluids removed from wound site 15 in response to the vacuum created at the wound site 15 by the negative pressure pump may pass through removed fluid tubing 50b and may be collected in removed fluid canister 240. In some embodiments, removed fluid canister 240 is detachable from therapy device 200 to allow removed fluid canister 240 to be emptied and replaced as needed.

b. Wound Dressing

Figure 2:
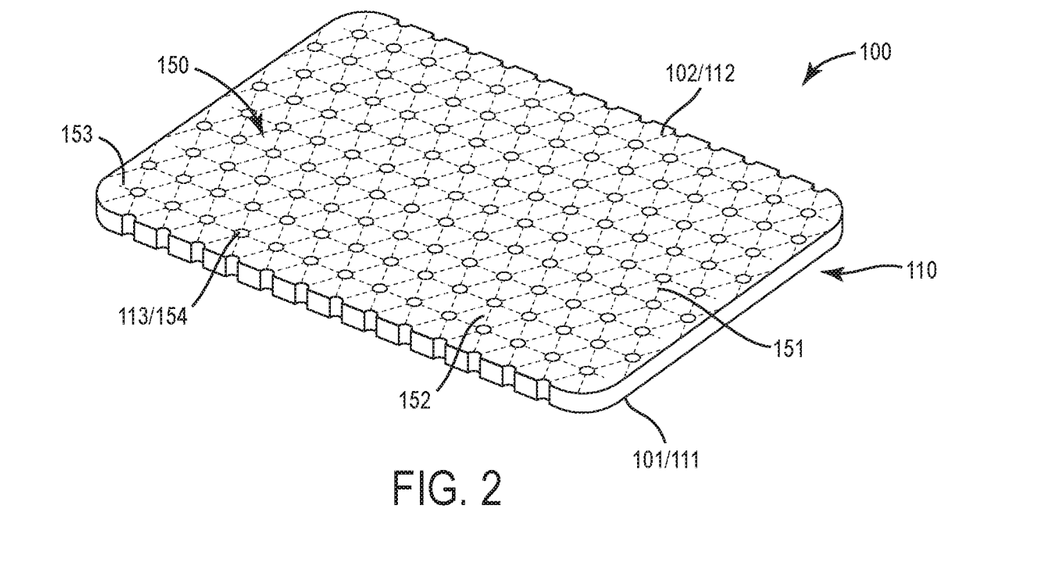
FIG. 2 is a top perspective view of a wound dressing according to one embodiment.
Figure 3A:
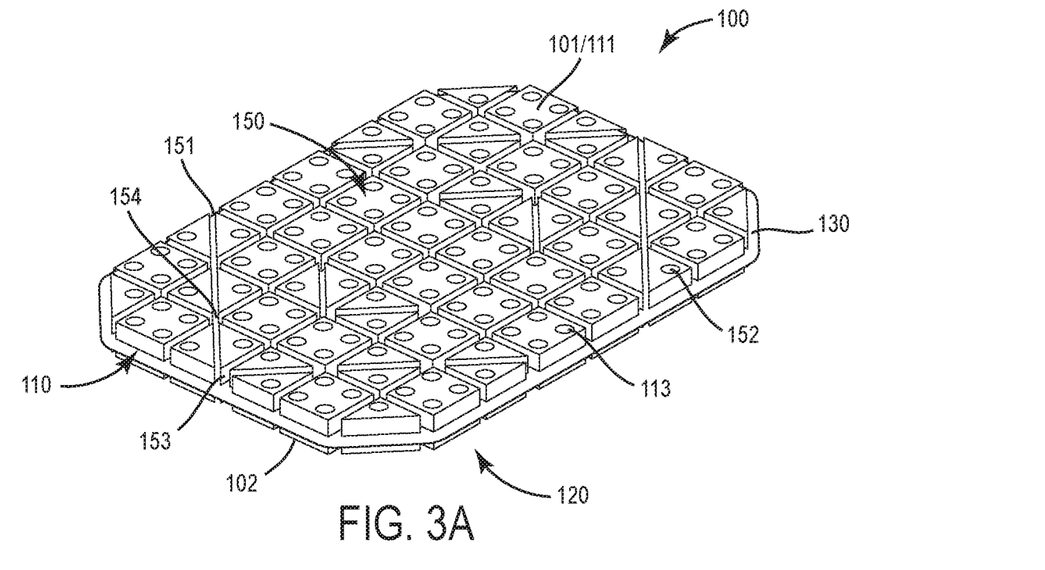
FIG. 3A is a top perspective view of a wound dressing according to one embodiment.
Figure 3B:
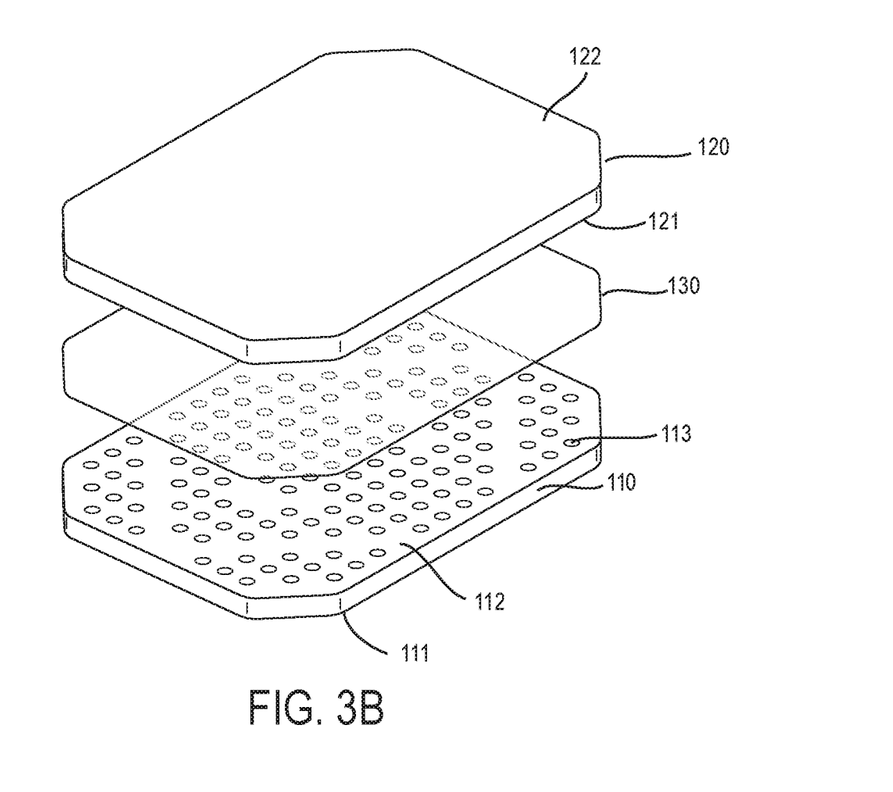
FIG. 3B is an exploded view of the wound dressing of FIG. 3A according to one embodiments.
Figure 4A:
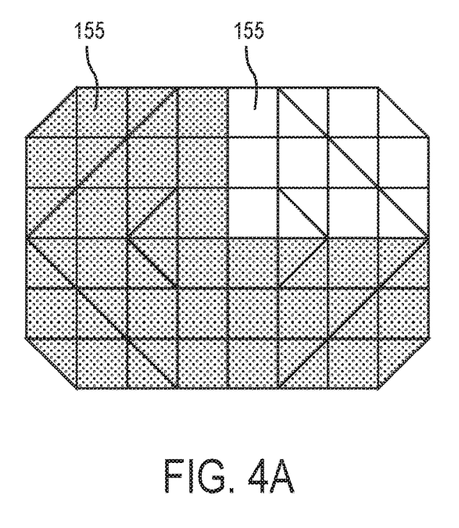
FIGS. 4A-4D are top views of wound dressings formed with visual aids according to various embodiments.
Figure 4B:
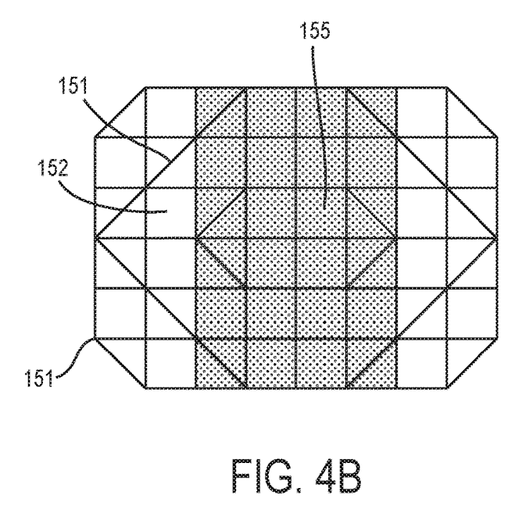
Figure 4C:
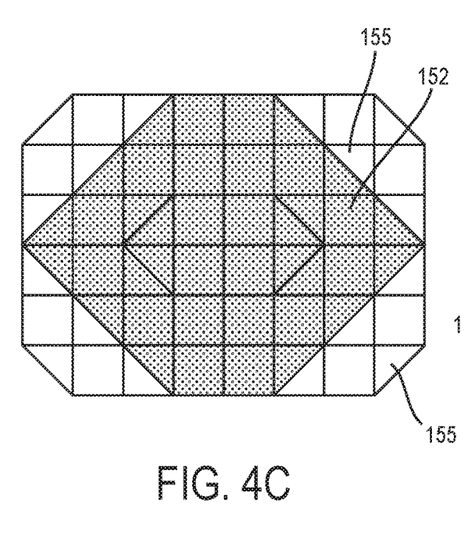
Figure 4D:
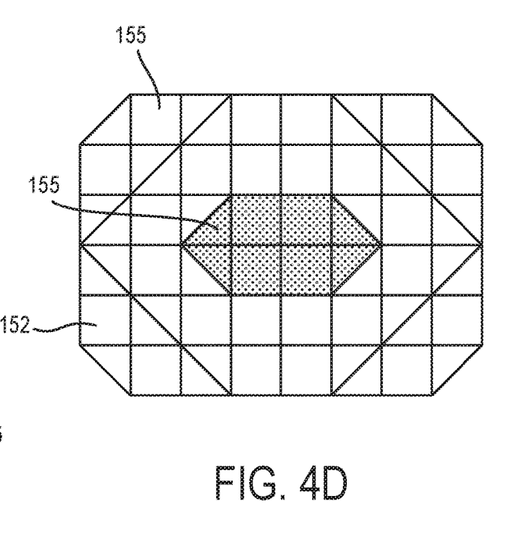

Referring to FIGS. 2-3B, in general, a manifold for placement in a wound, such as, e.g. wound dressing 100 may include a wound interface layer 110 configured to contact a wound site 15, as well as an optional cover layer 120 and/or optional film layer 130. According to various embodiments, the wound dressing 100 may at least partially be defined by a hydrophobic, open-cell foam. A drape layer 80 configured to attach the wound interface layer 110 to the patient's skin 10 surround the wound site 15.

As will be described in more detail below, the wound dressing 100 is formed having one or more intersecting structures 150 adapted to allow the size and shape of the wound dressing 100 to be easily and quickly customized based on the specific wound site 15 to which the wound dressing 100 is to be applied. As will also be described in more detail below, in addition to allowing for rapid, on-the-spot customization of the shape and size of the wound dressing 100, the intersecting structures 150 of the wound dressing 100 may provide for a simple estimation of wound site 15 volume, which may facilitate the calculation of the volume of instillation fluid to be applied to the wound site 15, and which may also allow the healing progress of the wound site 15 to be monitored.

Although the wound dressing 100 is configured to be customizable to the specific shape and size of the wound site 15 to be treated, the wound dressing 100 may be provided having any number of different initial configurations. By providing the wound dressing 100 in a variety of initial shapes and sizes, the amount of discarded wound dressing 100 material waste may be minimized. Additionally, by providing a user with a wound dressing 100 having an initial shape and size that already approximates the size and shape to that of the wound site 15, the amount of time and effort required to customize the configuration of the wound dressing 100 and to determine the volume of the resultant customized wound dressing 100 may be reduced.

i. Wound Interface Layer

The wound interface layer 110 is adapted to contact a wound site 15 along a lower, wound-facing surface 111 of the wound interface layer 110. In general, the wound interface layer 110 is formed from an absorbent material and is adapted to wick fluid (e.g. exudate) from the wound site 15.

Any number of bio-compatible materials may be used to construct the wound interface layer 110. A non-limiting, non-exhaustive list of the various materials that may be used to form the wound interface layer 110 may include: bioresorbable materials; materials configured to serve as a scaffold for new cell-growth, such as, e.g. calcium phosphate, collagen, hydrophobic open-cell foams, PLA/PGA, coral hydroxy apatites, carbonates, or processed allograft materials; thermoplastic elastomers; 3D textiles, also referred to as a spacer fabric, such as the 3D textiles produced by Heathcoat Fabrics, Ltd., Baltex, and Mueller Textil Group; foam, such as e.g. GranuFoam®, V.A.C. VeraFlo® foam, or V.A.C. WhiteFoam®, each available from Kinetic Concepts, Inc. of San Antonio, Tex., etc.

According to various embodiments, the materials used to form the wound interface layer 110, the properties of the wound-facing surface 111 and/or the configuration and structure of the wound-facing surface 111 may be selected to enhance the ability of the wound interface layer 110 to disrupt debris at the wound site 15. For example, in some embodiments, the wound-facing surface 111 may be formed of an abrasive material. In other embodiments, the wound-facing surface 111 may be defined by a textured surface having an uneven, coarse, or jagged profile that can induce strains and stresses at the wound site 15. In such embodiments, the wound-facing layer may be formed of an abrasive or non-abrasive material. In yet other embodiments, the wound interface layer 110 may be formed of an abrasive or non-abrasive compressible material, with the compression of the compressible material being adapted to increase the amount by which the wound-facing surface 111 is translated or oscillated laterally and/or longitudinally relative to the wound site 15 during treatment.

In various embodiments the wound-facing surface 111 of wound interface layer 110 may be formed having a generally solid, continuous, uninterrupted surface. In other embodiments, the ability of the wound interface layer 110 to disrupt debris at the wound site 15 may be enhanced via the selective removal of areas or portions of the wound-facing surface 111. For example, as illustrated in FIG. 3, according to various embodiments, the wound interface layer 110 may be constructed with a plurality of perforations or through-holes 113 extending entirely or partially through the wound interface layer 110 from the wound-facing surface 111 to an upper surface 112 of the wound interface layer 110.

The dimensions of the through-holes 113 may be varied as desired. While in some embodiments each of the through-holes 113 may have identical dimensions, in other embodiments the through-holes 113 may be formed having varied dimensions. Regardless of the dimensions selected for the through-holes 113, in embodiments in which the wound interface layer 110 is formed from a foam-like or other porous material, it is to be understood that the through-holes 113 do not include the pores of the material forming the wound interface layer 110, but rather are discrete perforations formed through the material forming the wound interface layer 110.

The through-holes 113 may be arranged about the wound interface layer 110 in any number of desired arrangements or patterns, including a random arrangement of the through-holes 113 about the wound interface layer 110. As illustrated in FIG. 3A, in some embodiments, the through-holes 113 may be arranged linearly, with adjacent rows of through-holes 113 optionally being offset from one another.

As shown in FIGS. 3A and 3B, in some embodiments, the through-holes 113 may have a circular shape. In other embodiments, the through-holes 113 may be formed having any number of other shapes, or any combination of different shapes, including, e.g. hexagonal, ovoid, or triangular shapes. When contracted, through-holes 113 having different cross-sectional shapes may generate and distribute concentrated stresses in different dimensions, and may accordingly influence disruption of debris in different ways. As such, in various embodiments the cross-sectional shape of the through-holes 113 may be based on the wound site 15 being treated and/or the degree of abrasion that may be desired at the wound site 15.

Regardless of the shape, size, arrangement, or degree to which the through-holes 113 extend through the wound interface layer 110, the through-holes 113 formed in the wound interface layer 110 define void spaces in the wound-facing surface 111. In response to the wound interface layer 110 being compressed, the voids provide spaces into which the wound-facing surface 111 is laterally and/or longitudinally collapsed. As the wound-facing surface 111 is compressed from its initial, relaxed configuration into the spaces defined by the voids, the lateral and/or longitudinal translation of the wound-facing surface 111 relative to the wound site 15 concentrates a shear force on the wound site 15 that allows for the disruption of the debris at the wound site 15.

ii. Cover Layer

As shown in FIGS. 3A and 3B, a cover layer 120 may optionally be coupled to the wound interface layer 110, with a wound-facing surface 121 of the cover layer 120 facing the upper surface 112 of the wound interface layer 110. The cover layer 120 may act as a manifold that is adapted to collect and/or distribute fluid and/or pressure across a wound site 15. For example, the cover layer 120 may be adapted to receive and distribute negative pressure across a wound site 15 to which the wound dressing 100 is applied, allowing for the wicking of fluid (e.g. exudate) from the wound site 15 and providing a distributed compressive force along the wound site 15. As another example, the cover layer 120 may also be used to facilitate the delivery of instillation fluid across a wound site 15. In wound dressing 100 embodiments incorporating an cover layer 120, the outer periphery of the cover layer 120 may be shaped and sized to generally correspond to, or optionally be smaller than, the outer periphery of the wound interface layer 110.

Any material or combination of materials might be used for the cover layer 120. In some embodiments, the cover layer 120 may comprise a porous and permeable foam layer, with the cover layer 120 being formed from a reticulated, open-cell polyurethane or polyether foam that allows good permeability of wound fluids while under a reduced pressure. In one non-limiting example, the cover layer 120 may be an open-cell, reticulated polyurethane foam such as GranuFoam® dressing available from Kinetic Concepts, Inc. of San Antonio, Tex. In other embodiments the cover layer 120 may be an open-cell, reticulated polyurethane foam such as a V.A.C. VeraFlo® foam, also available from Kinetic Concepts, Inc., of San Antonio, Tex. In yet other embodiments, the cover layer 120 may be formed of un-reticulated open-cell foam.

iii. Film Layer

As illustrated in FIGS. 3A and 3B, in various embodiments, the wound dressing 100 may optionally include a film layer 130. As will be discussed in more detail below, according to various embodiments the upper surface 112 of the wound interface layer 110 and—if included—the wound-facing surface 121 of the cover layer 120 may be laminated, adhered, mounted, or otherwise attached to the film layer 130 to minimize the shredding of the wound interface layer 110 and optional cover layer 120 during customization of the shape and size of the wound dressing 100.

According to various embodiments, the film layer 130 may be made of any number of elastic materials. For example, film layer 130 may be a polyurethane film, a polyethylene film, or other thin elastic. In other embodiments, the film layer 130 may be formed of any number of non-elastic materials. In some embodiments, film layer 130 may be substantially impermeable to liquid and substantially permeable to moisture vapor. In wound dressing 100 embodiments incorporating a film layer 130, the outer periphery of the film layer 130 may be shaped and sized to generally correspond to, or optionally be smaller than, the outer periphery of the wound interface layer 110.

The film layer 130 may be adapted to elastically deform upon application of a stretching force to the wound dressing 100. For example, in some embodiments, the film layer 130 may be designed to elastically stretch when a stretching force is applied and elastically recover when the stretching force is removed. In other words, film layer 130 may be configured to exhibit substantially elastic deformation and recovery.

According to various embodiments, film layer 130 may optionally include one or more fenestrations 131 adapted to allow for the transfer of fluids (e.g. instillation fluid) and pressure to/from the wound interface layer 110. The fenestrations 131 may also be adapted to reduce the amount of force required to stretch film layer 130. In embodiments in which the wound interface layer 110 is defined by through-holes 113, the spacing, sizing, and arrangement of the fenestrations 131 may optionally correspond to the spacing, sizing and arrangement of the through-holes 113 of the wound interface layer 110.

iv. Intersecting Structure

Referring to FIGS. 2, 3A, and 4A-4D, according to various embodiments, the wound dressing 100 is formed being defined by an intersecting structure 150. The intersecting structure 150 is defined by a plurality of interconnected separation-lines 151 arranged about the lower surface 101 and/or upper surface 102 of the wound dressing 100 in a pattern to define a plurality of discrete blocks 152. In general, the shape and size of the wound dressing 100 may be modified to conform to the shape and size of the wound dressing 100 via the selective removal of one or more discrete blocks 152 along the one or more separation-lines 151 bounding the discrete block(s) 152 that are to be removed.

According to various embodiments, the separation-lines 151 forming the intersecting structure 150 may be defined by one or more weakened portions 153 configured to allow for easy, precise, rapid and tool-free (i.e. entirely manual) detachment of one or more desired blocks 152 from the remaining portion of the wound dressing 100. These weakened portions 153 may comprise any number of and any combination of interspaced perforations, slits, holes, scores, tear-lines, markings, delineations or any other number of different structures which may be configured to decrease the force required to detach adjacent blocks 152 along the separation-lines 151. According to some embodiments, the weakened portions 153 may extend entirely through the wound dressing 100 from an upper surface 102 to a lower surface 101 of the wound dressing 100 (i.e. defining a through-hole or passageway through the wound dressing 100). In other embodiments, the weakened portions 153 may extend partially through the wound dressing 100 from the upper surface 102 towards an interior of the wound dressing and/or from the lower surface 101 towards the interior of the wound dressing 100 (i.e. defining thinned sections of the wound dressing 100, but not defining passageway through the wound dressing 100).

As noted above, wound dressing 100 may be formed having any number of different layers, including a wound interface layer 110 and optional cover layer 120. As also discussed above, according to various embodiments, the wound interface layer 110 and cover layer 120 may each be formed from foam-like materials. Given the tendency of foam-like materials (such as, e.g. those that may be used to form wound interface layer 110 and/or cover layer 120) to shred/crumble in response to being torn, according to various embodiments, it may be advantageous to incorporate a film layer 130 that may be configured to minimize or prevent the shredding/crumbling of the foam-like material forming the wound interface layer 110 and optional cover layer 120.

In some embodiments in which a film layer 130 is incorporated, such as, e.g. illustrated in FIG. 3A, the wound interface layer 110 and optional cover layer 120 may be formed with weakened portions 153 extending partially or entirely through the wound interface layer 110 and/or option cover layer 120, with the lamination, mounting, or other attachment of the wound interface layer 110 and option cover layer 120 to the film layer 130 being configured to stabilize the structure of the wound interface layer 110 and optional cover layer 120 and thereby minimize or prevent the shredding/crumbling of the wound interface layer 110 and optional cover layer 120 upon detachment of blocks 152 along the separation-lines 151. In some such embodiments, the weakened portions 153 of the separation-lines 151 may extend through the film layer 130, while in other embodiments, the film layer 130 may be formed without the weakened portions 153 passing therethrough (i.e. the film layer 130 may be formed free of any disruptions therethrough besides the optionally included fenestrations 131).

According to other embodiments, the risk of shredding/crumbling of the foam-like materials forming the wound interface layer 110 and optional cover layer 120 may be further minimized or even eliminated by welding or otherwise affixing those portions of the wound interface layer 110 and optional cover layer 120 that are to define the separation-lines 151 to the film layer 130, such as, e.g. illustrated by the embodiment of wound dressing 100 of FIG. 3A, with the foam-like materials forming the wound interface layer 110 and optional cover layer 120 being compressed and condensed about those portion of the wound interface layer 110 and optional cover layer 120 that are welded or otherwise affixed to the film layer 130 to define the separation-lines 151. The compression/compaction resulting from the welding or other affixation of the wound interface layer 110 and optional cover layer 120 to the film layer 130 allows the detachment forces to be distributed more evenly through the separation-line 151 defined wound interface layer 110 and optional cover layer 120, thereby minimizing the risk of the wound interface layer 110 and optional layer from shredding/crumbling as the wound dressing 100 is detached along the separation-lines 151. In such embodiments, the weakened portions 153 of the separation-lines 151 may pass partially or entirely through one, all, or a combination of the film layer 130, the compressed, separation-line 151 portion of the wound interface layer 110 and/or the compressed, separation-line 151 portion of the cover layer 120. According to some embodiments, the portions of the wound interface layer 110 and optional cover layer 120 defining the blocks 152 and/or other portions of the wound dressing 100 may also be laminated, mounted or otherwise attached to the film layer 130. Although the film layer 130 in FIG. 3B is shown as being formed without any fenestrations 131, it is to be understood that in other embodiments, film layer 130 may include one or more fenestrations extending therethrough.

Although in the embodiment of wound dressing 100 shown in FIGS. 3A and 3B the film layer 130 is shown being welded to both the wound interface layer 110 and the cover layer 120, according to other embodiments, the film layer 130 may optionally be welded to one of the wound interface layer 110 and the cover layer 120, with the film layer 130 being laminated, mounted or otherwise attached to the other of the wound interface layer 110 and cover layer 120. In yet other embodiments, instead of (or in addition to) film layer 130 being positioned in between and welded to one or both of the wound interface layer 110 and cover layer 120, the film layer 130 may alternatively be welded to portions of an upper surface 122 of the cover layer, with the wound-facing surface 121 of the cover layer 120 being laminated, mounted or otherwise attached to the wound interface layer 110 (or additional, optional film layer 130).

In yet another embodiment (not shown), the risk of the foam-like materials forming the wound interface layer 110 and optional cover layer 120 shredding/crumbling may be entirely eliminated by forming the wound interface layer 110 and optional cover layer 120 as a plurality of individual, discrete blocks 152 which are laminated, mounted, adhered, or otherwise attached to the film layer 130 in the spaces bounded by intersection separation-lines 151 defined by weakened portions 153 that are formed on the film layer.

The separation-lines 151 may be formed about the wound dressing 100 in any desired pattern, with the separation-lines 151 intersecting one another at any desired angle or combination of angles. The blocks 152 defined between separation-lines 151 may be formed having any number of different shapes and/or sizes as desired. For example, in some embodiments, the arrangement of the separation-lines 151 may be used to define a plurality of uniformly sized and shaped blocks 152, while in other embodiments the arrangement of the separation-lines 151 may results in blocks 152 of differing shapes and/or sizes, such as the combined rectangular and triangular blocks 152 of the wound dressing 100 embodiments of FIG. 3A. As will be understood, regardless of whether the individual blocks 152 are uniform or vary in shape and/or size, each block 152 will have a predetermined, known volume that the user is provided by which the user can calculate the volume of the final, customized wound dressing 100.

The ease with which adjacent blocks 152 may be detached from one another along the separation-lines 151 may be based on a number of variables, such as, e.g., the structure/configuration of the weakened portions 153, the degree to which the weakened portions 153 extend through the wound dressing 100, the thickness and material forming the part of the wound dressing 100 through which the weakened portions 153 extend, etc. As will be understood, any of these or other variables affecting the ease with which adjacent blocks 152 may be detached from one another along the separation-lines 151 may be varied as desired to provide a wound dressing 100 having separation-lines 151 that detach upon application of as little or as much force as desired.

Additionally, in some embodiments, it may be desired to provide separation-lines 151 requiring varying degrees of force to detach one or more blocks 152 forming the wound dressing 100. For example, in some embodiments, longer length separation-lines 151 that traverse the entirety of or a large portion of the length of the wound dressing 100 may be configured such that a greater force is required to detach the longer length separation-lines 151 than is needed to detach shorter length separation-lines 151 that traverse only short portions of the wound dressing 100. In such embodiments, the higher force required to detach the longer length separation-lines 151 may be configured to prevent accidental separation of a large portion of blocks 152, while the lower force required to detach shorter length separation-lines 151 may be configured to allow for a more precise removal of individual blocks 152. As will be understood, in other embodiments, the arrangement of separation-lines 151 having differing minimum detachment force thresholds about the wound dressing 100 may be based on any number of other variables, and may be varied as desired.

According to various embodiments, in addition to or as an alternative to varying the force required to detach separation-lines 151, the intersecting structure 150 may include one or more stop points 154 at any number of desired intersections of the separation-lines 151 defining the intersecting structure 150. As shown in FIGS. 2 and 3A, the stop points 154 are may comprise any number of and any combination of perforations, slits, holes, scores, tear-lines, markings, delineations or any other number of different structures that extend partially or entirely through the wound dressing 100, with the dimensions of the stop point 154 being generally greater than the dimensions of the perforations, slits, holes, scores, tear-lines, markings, delineations, etc. that define the weakened portions 153 defining separation-lines 151. As such, as adjacent blocks 152 are being separated along a separation-line 151, the incorporation of a stop point 154 along the separation-line 151 at a junction defining an edge of the blocks 152 may provide tactile feedback which can signify to a user that a junction between adjacent blocks 152 has been reached. Referring to FIG. 2, in some embodiments in which the wound interface layer 110 includes one or more through-holes 113, the intersecting structure 150 may be arranged such that the stop points 154 are defined by the through-holes 113.

In addition to facilitating and allowing for tool-free customization of the shape and size of a wound dressing 100, the intersecting structure 150 of the wound dressing 100 also provides a quick and easy manner in which the volume of a wound site 15 may be calculated. For example, during instillation therapy, such as e.g. provided by the therapy device 200 of FIG. 1, it may be desirable to know the volume of the wound site 15 that is being treated, so that a reliably predictable volume of instillation fluid may be delivered to the wound site 15 in a quantity sufficient to adequately and properly achieve the desired effect on the wound site 15 without over-delivering fluid to the wound site 15, which could adversely affect the ability of the drape layer 80 to maintain the desired seal with the patient's skin 10. Accordingly, by providing a way by which the wound dressing 100 can be used to estimate volume of the wound site 15 in which the wound dressing 10 is being placed, the wound dressing 100 may provide for an improved instillation therapy method.

In general, the wound dressing 100 is configured such that the volume of a wound tissue site 15 may be calculated by subtracting the number of discrete blocks 152 that have been removed during wound dressing 100 customization from the initial number of discrete blocks 152 forming the wound dressing 100 and/or by counting the number of discrete blocks 152 that remain following wound dressing 100 customization and multiplying the calculated number of remaining discrete blocks 152 defining the resultant wound dressing 100 by the known volume of each discrete block 152.

Although the step of determining the number of discrete blocks 152 defining the resultant customized wound dressing 100 may be performed through a manual counting of individual blocks 152, according to various embodiments, the wound dressing 100 may be configured with any number of and any combination of visual aids that may allow for a quick determination of remaining discrete blocks 152 without requiring the counting of each of the individual blocks 152 detached from the wound dressing 100.

For example, according to various embodiments, such as, e.g. illustrated in FIGS. 4A-4D, the discrete blocks 152 defining the wound dressing 100 may be divided up into one or more sections 155 define by a plurality of discrete blocks 152, with each section 155 being visually distinguishable (e.g. via the use of different colors, different logos, by separating adjacent sections 155 using separation-lines 151 that are a different thickness/width than that of separation-lines 151 extending between blocks 152 within the same section 155, etc.) from other sections 155. In some such embodiments, the various sections 155 may be formed having identical shapes and/or sizes or may be formed having differing shapes and/or sizes. Although in such embodiments the wound dressing 100 may still be customized through the selective removal of individual blocks 152, by grouping the wound dressing 100 into sections 155, the number of individual removed blocks 152 that the user need keep track of is reduced.

In embodiments of wound dressing 100 incorporating a wound interface layer 110 and a cover layer 120, according to some embodiments, differing visual aids may be incorporated on the wound interface layer 110 and cover layer 120, even though the division of the wound interface layer 110 into discrete blocks 152 is mirrored by the division of the cover layer 120 into discrete blocks 152. For example, although the blocks 152 defining both the wound interface layer 110 and the cover layer 120 may be divided up into sections 155 as described above, the arrangement of sections 55 of blocks 152 on the wound interface layer 110 may vary from the arrangement of section 155 on the cover layer 120. In such embodiments, the user may select which arrangement of sections 155 of blocks 152 conforms more closely to the shape and size of the wound site 15 (i.e. would require the user to tear away the least amount of individual, discrete blocks 152), and use that section 155 arrangement as a guide to customize the wound dressing 100 and estimate volume. Regardless of which side the sections 155 (i.e. wound interface layer 110 or cover layer 120) the user relied on in customizing the wound dressing 100, it is to be understood that the wound dressing 100 would be positioned in the wound site 15 with the wound interface layer 110 interfacing the wound site 15.

As will be understood, although the above-described wound dressing 100 features that are configured to allow a user to quickly and easily estimate or determine the volume of a wound site 15 are described as being used with a wound dressing 100 formed having an intersecting structure 150 configured to allow for tool-free customization of the shape and size of the wound dressing 100, it is to be understood that in some embodiments (not shown), the wound dressing 100 features described herein for calculating the volume of a wound site 15 may also be used with wound dressing 100 embodiments in which the wound dressing 100 is formed without an intersecting structure 150. In such embodiments, instead of a plurality of separation-lines 151 extending at least partially through the wound dressing 100 to define a plurality of detachable blocks 152, one or more markings may instead be formed about an upper surface 102 and/or lower surface 101 of the wound dressing 100. Similar to separation-lines 151, the markings are intended to delineate borders between adjacent blocks 152, with the markings indicating to a user where to cut the wound dressing 100 to achieve a wound dressing 100 having a desired shape, size and calculable volume.

As will be understood, the volume of fluid that the wound dressing 100 is configured to retain (e.g. the amount of instillation fluid that may be delivered to the wound dressing 100 without resulting in overflow) is less than the calculated volume of the customized wound dressing 100. Accordingly, once a user has determined the volume of a customized wound dressing 100, the volume may be multiplied by an appropriate fluid instillation factor to calculate the amount of instillation fluid that is to be instilled from the instillation fluid canister 210 of the therapy device 200 in order to avoid over-saturating the wound dressing 100. According to various embodiments, the fluid instillation factor may be within a range of between approximately 0.10 and 1.00.

The selection of fluid instillation factor may be influenced by a variety of factors. According to various embodiments, the selection of fluid instillation factor may be based at least in part on the known maximum amount of fluid that an initially uncompressed, dry, and completely unsaturated wound dressing 100 may retain prior to the wound dressing 100 becoming oversaturated with fluid such that fluid is not absorbed by the wound dressing 100. Among other factors, this maximum volume of fluid that can be retained by the wound dressing 100 may be based on, e.g., the type of material(s) used to form the wound dressing 100, the density of the layers forming the wound dressing 100, the porosity of the layers of the wound dressing 100, whether or not through-holes 113 are formed in the wound dressing 100, etc. For example, embodiments in which the wound dressing 100 is made of a less dense material may be capable of retaining more fluid than embodiments in which the wound dressing 100 is made of a dense material, with the less dense wound dressing 100 embodiments accordingly being assigned a higher fluid instillation factor than denser wound dressing 100. As will also be understood, in wound dressing 100 embodiments incorporating more than one layer of foam-like material (e.g. including a cover layer 120), the fluid instillation factor will be based on the combined properties of each of the layers forming the wound dressing 100.

Given that the wound dressing 100 is configured to allow a user to customize the shape and size of the wound dressing 100 as desired, according to various embodiments, a user may be provided with information regarding the maximum volume of fluid that each individual block 152 forming the wound dressing 100 may retain. The user can then use this information to calculate the total maximum volume of fluid that the resultant, customized wound dressing 100 may retain based on the calculated number of blocks 152 defining the customized would dressing 100. Alternatively, or additionally, the user may be provided with the maximum volume of fluid capable of being retained by the initially provided wound dressing 100 as well as the initial volume of the wound dressing 100, with the user subsequently multiplying the provided maximum volume of fluid capable of being retaining by the initial, non-customized wound dressing 100 by the percent reduction of volume of the wound dressing 100 following wound dressing 100 customization (i.e. calculated resultant, customized wound dressing 100 volume divided by the initial volume of the wound dressing 100 prior to customization). As will be understood, according to various embodiments, the information regarding maximum retained fluid volume, original wound dressing 100 volume, etc. may be provided to, stored by, and utilized by the controller 300 to provide the user with the relevant information.

According to some embodiments, in addition to, or as an alternative to, allowing a user to calculate instillation fluid volume to be delivered to the wound site 15, the customizable wound dressing 100 may allow a user to monitor the healing of the wound site 15 over time. In particular, according to various treatment regimens, the wound dressing 100 may be changed one or more times over the course of wound site 15 treatment using the wound therapy system 1. Each time that a new wound dressing 100 is replaced, the volume of the new customized wound dressing 100 may be monitored, with the progress of wound site 15 healing being reflected by the degree of wound site 15 volume decrease that is measured.

Figure 5:
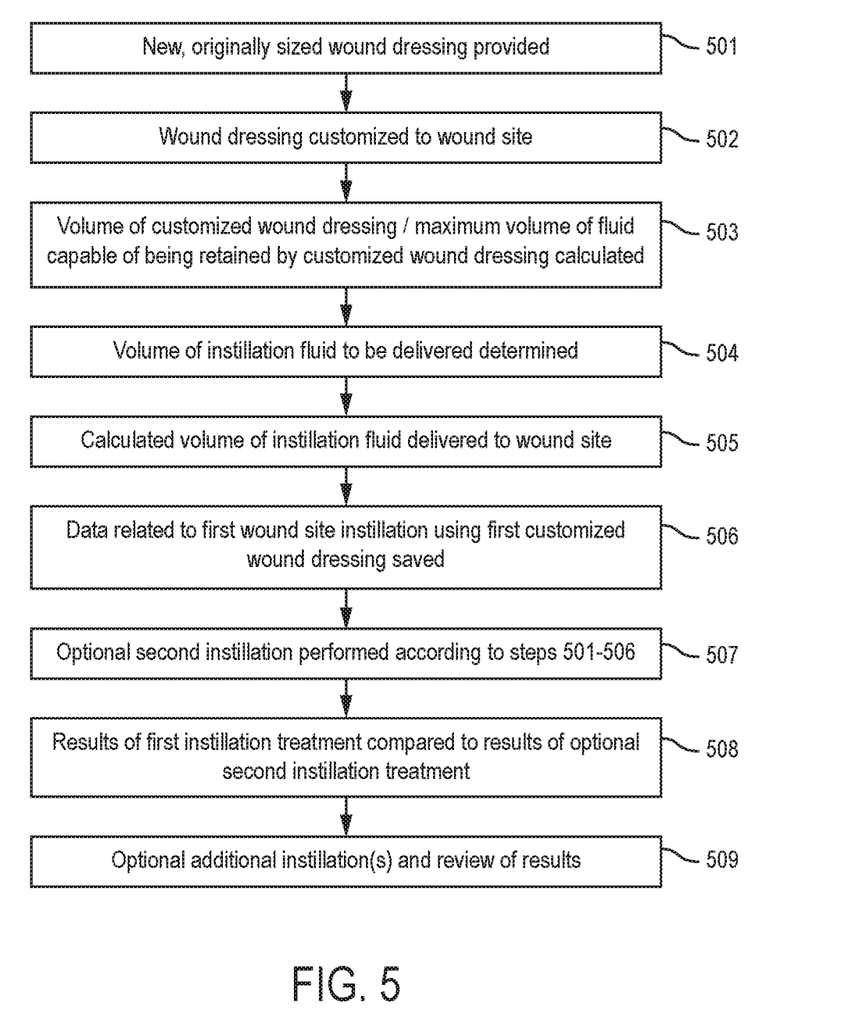
FIG. 5 illustrates a flowchart for monitoring wound healing progression according to one embodiment.

Referring to FIG. 5, a flow chart representative of the method by which the wound dressing 100 may be used to monitor the healing of the wound site 15 over time is illustrated. At step 501, the user is provided with a wound dressing 100 in a dry, uncompressed, and unsaturated state that is defined by an intersecting structure 150 formed of a plurality of discrete blocks 152. The user may optionally be provided with the initial volume of the wound dressing 100 and/or the maximum volume of fluid that the originally-sized wound dressing 100 is configured to retain. This information may be provided to the user in the form of a chart, or may be provided in the form of software that is capable of being executed by the controller 300 of a therapy device 200 with which the wound dressing 100 is configured to be used and/or by any other computer device that the user may wish to utilize to monitor the wound healing process.

At step 502, the user customizes the initially provided wound dressing 100 to the size and shape of the wound site 15 that is to be treated through the selective removal of one or more blocks 152 along separation-lines 151. As discussed above, in some embodiments where significant portions of the wound dressing 100 are to be removed, the user may expedite the process of customizing the wound dressing 100 by removing larger, sectioned-off and pre-defined portions of the wound dressing 100 (e.g. sections 155 or along separation-lines 151 requiring varying degrees of force to detach adjacent blocks 152). Once the wound dressing 100 has been modified to a shape and size generally in conformity with the wound site 15, the user may proceed with a more fine-tuned, and precise customization of the wound dressing 100 by the selective removal of individual blocks 152.

Once the wound dressing 100 has been tailored to the wound site 15, at step 503 the volume of the resultant wound dressing 100 and/or the maximum volume of fluid that the resultant wound dressing 100 is configured to retain may be determined by calculating the number of blocks 152 defining the resultant wound dressing 100. As discussed above, the remaining number of blocks 152 defining the wound dressing 100 may be determined by subtracting the number of blocks 152 that were selectively removed from the initial total number of blocks 152 forming the originally-sized wound dressing 100 and/or by counting the number of blocks 152 that define the resultant, customized wound dressing 100.

Once the number the volume of and/or the maximum volume of fluid that may be retained by the customized wound dressing 100 has been determined (either directly by the user or by the controller 300 or other computer device utilized by the user), an amount of fluid to be instilled into the customized wound dressing 100 may be determined at step 504. According to various embodiments, the amount of fluid to be instilled may be based multiplying the volume of the customized wound dressing 100 and/or the maximum volume of fluid that may be retained by the customized wound dressing 100 by a fluid instillation factor.

In particular, in embodiments in which the fluid instillation factor is to be applied to a total volume of the customized wound dressing 100 as calculated at step 503, the selected fluid instillation factor may be configured to account for differences in in the materials, densities, porosities, etc. that define different wound dressings 100. Accordingly, in such embodiments, the user may be provided (either as a chart or in the form of executable software) with a relationship between the specific type of wound dressing 100 being utilized (e.g. number of layers, types of layers, etc. defining the wound dressing 100) and an appropriate fluid instillation factor. In embodiments in which the maximum volume of fluid that may be retained by the customized wound dressing 100 has been calculated at step 503, the fluid instillation factor may be selected, e.g. based on the percentage of the fluid capacity of the customized wound dressing 100 that the user wishes to utilize during treatment of the wound site 15.

According to various embodiments, in addition to, or as an alternative to, applying a fluid instillation factor to the calculated total customized wound dressing volume 100 and/or the calculated maximum volume that the customized wound dressing 100 is capable of retaining to determine the volume of fluid to be instilled, a correction factor may additionally be subtracted when calculating the volume of instillation fluid that is to be delivered to the wound site 15. Such a correction factor may be used to prevent over-instillation of the wound dressing 100.

As shown in step 505, the volume of instillation fluid calculated at step 504 is delivered to the wound site 15. According to various embodiments, the volume of instillation fluid may be delivered from the instillation fluid canister 210 of the therapy device 200, and may optionally be controlled via the controller 300. At optional step 506, information and data regarding the calculated volume of the resultant wound dressing 100 and/or the maximum volume of fluid that the resultant wound dressing 100 is configured to retain, the calculated amount of fluid to be instilled into the customized wound dressing 100 determined at step 504, and/or the actual volume of fluid instilled at step 505 may be recorded by a user and/or saved by the controller 300.

According to various embodiments, treatment of a wound site 15 may require that the wound dressing 100 at the wound site 15 be periodically replaced. Accordingly, after the data from the first instillation using the first wound dressing 100 has been appropriately stored at step 506, a second instillation using a second wound dressing 100 may be performed at step 507, with the process of the second instillation using a second wound dressing 100 being generally identical to the processes described in steps 501 through 506 with regards to the first instillation using the first wound dressing 100.

At step 508, once the data from the second instillation using the second wound dressing 100 has been stored, the stored data from the first and second instillations may be compared to one another, with the change in wound site volume 15 (as, e.g. reflected by the change in calculated total customized wound dressing volume 100) allowing a user to gauge the amount by which the wound site 15 has healed. The results of this comparison may optionally be saved by the controller 300 and/or recorded by the user as part of step 508.

As will be understood, at step 509, steps 501 through 508 can be repeated for any number of additional instillations using new wound dressings 100, with the additional data acquired during these steps allowing a user to continue monitoring wound healing progress (as, e.g. reflected by the change in calculated total customized wound dressing 100 volume, the rate of change of calculated total customized wound dressing 100 volume, etc.). According to various embodiments, the additional instillations and monitoring/comparisons of said additional instillations at step 509 may be performed until a predetermined goal (e.g. a target wound site 15 volume, a target rate of wound site 15 volume decrease, number of recorded data reference points, etc.) has been achieved, at which point treatment using the therapy device 200 may be discontinued.

In some embodiments, the results of and data from the treatment using the therapy device 200 may be stored by the user and/or controller 300, such that future treatments using the therapy device 200 may use the obtained data as reference points to monitor the progress of new treatments. For example, in some embodiments, a monitored rate of change of calculated total customized wound dressing 100 volume that decreases at a rate lower than a stored rate of change of calculated total customized wound dressing 100 volume may indicate to a user that treatment of the wound site 15 may need to be re-evaluated.

c. Controller

According to various embodiments, the wound treatment system 1 may include an optional controller 300. The controller 300 may be configured to operate negative pressure pump, instillation pump, and/or other controllable components of wound therapy system 1.

In some embodiments, the controller 300 may be programmed to assist the use in calculating the volume of the resultant customized wound dressing 100. For example, in wound dressing 100 embodiments in which the blocks 152 are divided into one or more sections 155, the controller 300 may ask the user to input the sections 155 and the number of discrete individual blocks 152 removed during wound dressing 100 customization, with the controller 300 being able to automatically calculate the volume of the wound dressing 100 based on the input information. Additionally, the controller 300 may be configured to determine an appropriate fluid instillation factor based on input from a user regarding the type of wound dressing 100 (i.e. number and types of layers, materials used to form layers, etc.). Furthermore, the controller may be configured to store information regarding the wound site 15 treatment protocol (e.g. number of wound dressing changes 100, time in between wound dressing 100 changes, size of wound dressing 100, etc.) with the controller 300 being capable of being used to determine healing progression based on changes in these stored values (e.g. changes in wound volume during wound treatment).

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

We claim:

1. A wound therapy system comprising:
   a manifold for placement in a wound comprising a plurality of perforations that divide the manifold into a plurality of discrete blocks and facilitate separating one or more of the discrete blocks from a remainder of the discrete blocks along the perforations, wherein each of the plurality of discrete blocks has a known volume of fluid it can hold when uncompressed; and
   a drape layer configured for placement over the manifold and wound to create a sealed space;
   a therapy device operable to deliver negative pressure to the sealed space;
   a user interface configured to receive user input, wherein said user input is the number of discrete blocks that have been placed in the wound; and
   a controller configured to determine a volume of the instillation fluid to deliver to the sealed space based on the user input.

2. The wound therapy system of claim 1, wherein the controller determines the volume of instillation fluid to deliver by:
   multiplying the number of blocks that have been placed in the wound with the known volume of fluid each block can hold when uncompressed; and
   subtracting a correction factor to avoid over-instillation.

3. The wound therapy system of claim 1, wherein:
   the manifold comprises a wound interface layer configured to contact a wound; and
   the plurality of intersecting perforations extend through the wound interface layer.

4. The wound therapy system of claim 3, wherein:
   the manifold comprises a cover layer coupled to the wound interface layer; and
   the plurality of intersecting perforations extend through both the cover layer and the wound interface layer.

5. The wound therapy system of claim 1, wherein the manifold comprises: a wound interface layer configured to contact a wound;
   a cover layer coupled to the wound interface layer; and a plurality of holes that extend through the wound interface layer and the cover layer.

6. The wound therapy system of claim 5, wherein the plurality of holes are located at intersections of the plurality of intersecting perorations.

7. The wound therapy system of claim 5, wherein the plurality of holes are located within the plurality of discrete blocks offset from the plurality of intersecting perforations.

8. The wound therapy system of claim 1, wherein the plurality of discrete blocks comprise:
at least one triangular block; and
at least one rectangular block.

9. The wound therapy system of claim 1, wherein the controller is configured to use the number of the discrete blocks separated from the remainder of the discrete blocks to determine the volume of the instillation fluid to deliver to the manifold.

10. The wound therapy system of claim 1, wherein:
the user input indicates both the number of the discrete blocks separated from remainder of the discrete blocks and a type of the manifold; and
the controller is configured to use both the number of the discrete blocks separated from remainder of the discrete blocks and the type of the manifold to determine the volume of the instillation fluid to deliver to the manifold.

11. The wound therapy system of claim 1, wherein the controller is configured to:
estimate a wound volume based on the number of discrete blocks indicated by the user input; and
determine the volume of instillation fluid to deliver to the manifold based on the estimated wound volume.

12. The wound therapy system of claim 11, wherein the controller is configured to:
estimate the wound volume at a plurality of times during wound treatment; and determine healing progression based on changes in the estimated wound volume during wound treatment.

13. The wound therapy system of claim 12, wherein the controller is configured to determine the volume of instillation fluid to deliver to the manifold by multiplying the estimated wound volume by a fluid instillation factor.

14. The wound therapy system of claim 13, wherein the fluid instillation factor is less than one such that less than a total volume of the manifold is filled with the instillation fluid.

15. A wound therapy system comprising:
a wound dressing comprising a plurality of intersecting delineations that divide the wound dressing into a plurality of discrete blocks and facilitate separating one or more of the discrete blocks from a remainder of the discrete blocks along the delineations; and
a therapy device comprising:
a pump operable to deliver an instillation fluid to the wound dressing;
a user interface configured to receive user input indicating a number of the one or more discrete blocks separated from the remainder of the discrete blocks; and
a controller configured to determine a volume of the instillation fluid to deliver to the wound dressing based on the user input and to operate the pump to deliver the determined volume of the instillation fluid to the wound dressing.

16. The wound therapy system of claim 15, wherein the plurality of intersecting delineations comprise welds that extend at least partially through the wound dressing.

17. The wound therapy system of claim 15, wherein the controller is configured to use the number of the discrete blocks separated from the remainder of the discrete blocks to determine the volume of the instillation fluid to deliver to the wound dressing.

18. The wound therapy system of claim 15, wherein:
the user input indicates both the number of the discrete blocks separated from remainder of the discrete blocks and a type of the wound dressing; and
the controller is configured to use both the number of the discrete blocks separated from remainder of the discrete blocks and the type of the wound dressing to determine the volume of the instillation fluid to deliver to the wound dressing.

19. A method for delivering instillation fluid to a wound, the method comprising: separating one or more discrete blocks of a wound dressing from a remainder of the discrete blocks along delineations of the wound dressing;
receiving user input indicating a number of the discrete blocks separated from the remainder of the discrete blocks at a user interface of a wound therapy device;
determining, by the wound therapy device, a volume of instillation fluid to deliver to the wound dressing based on the user input; and
operating a pump of the wound therapy device to deliver the determined volume of the instillation fluid to the wound.

20. The method of claim 19, further comprising using the number of the discrete blocks separated from the remainder of the discrete blocks to determine the volume of the instillation fluid to deliver to the wound dressing.

21. The method of claim 19, further comprising:
estimating a wound volume based on the number of discrete blocks indicated by the user input; and
determining the volume of instillation fluid to deliver to the wound dressing based on the estimated wound volume.

22. The method of claim 21, further comprising:
estimating the wound volume at a plurality of times during wound treatment; and determining healing progression based on changes in the estimated wound volume during wound treatment.

23. The method of claim 21, wherein determining the volume of instillation fluid to deliver to the wound dressing comprises multiplying the estimated wound volume a fluid instillation factor.

* * * * *

UNITED STATES PATENT AND TRADEMARK OFFICE
CERTIFICATE OF CORRECTION

PATENT NO. : 11,628,094 B2
APPLICATION NO. : 17/253263
DATED : April 18, 2023
INVENTOR(S) : Justin Rice

Page 1 of 1

It is certified that error appears in the above-identified patent and that said Letters Patent is hereby corrected as shown below:

In the Claims

<u>Column 21</u>
Line 5, In Claim 6, delete "intersecting perorations" and insert -- intersecting perforations --, therefor.

Signed and Sealed this
Ninth Day of April, 2024

Katherine Kelly Vidal
*Director of the United States Patent and Trademark Office*